United States Patent
Dembro

(10) Patent No.: US 8,201,560 B2
(45) Date of Patent: Jun. 19, 2012

(54) FLEXIBLE DENTAL APPLIANCE

(76) Inventor: Jay L. Dembro, Pocassett, MA (US)

( * ) Notice: Subject to any disclaimer, the term of this patent is extended or adjusted under 35 U.S.C. 154(b) by 152 days.

(21) Appl. No.: 11/901,818

(22) Filed: Sep. 19, 2007

(65) Prior Publication Data

US 2008/0066768 A1 Mar. 20, 2008

Related U.S. Application Data

(60) Provisional application No. 60/845,789, filed on Sep. 19, 2006.

(51) Int. Cl.
A61C 5/14 (2006.01)
A61C 3/00 (2006.01)

(52) U.S. Cl. .................. 128/861; 433/6; 433/7

(58) Field of Classification Search .............. 128/848, 128/856–862; 602/902; 433/6, 7, 34, 37, 433/41–44, 140; 604/77
See application file for complete search history.

(56) References Cited

U.S. PATENT DOCUMENTS

| | | | |
|---|---|---|---|
| 3,532,091 A | 10/1970 | Lerman | 128/136 |
| 3,924,638 A | 12/1975 | Mann | 128/359 |
| 4,457,708 A | 7/1984 | Dufour | 433/6 |
| 4,519,386 A | 5/1985 | Sullivan | 128/136 |
| 4,671,766 A | 6/1987 | Norton | 433/6 |
| 4,799,500 A | 1/1989 | Newbury | 128/859 |
| D300,059 S | 2/1989 | Pier | D24/10 |
| 5,052,409 A | 10/1991 | Tepper | 128/859 |
| 5,092,346 A * | 3/1992 | Hays et al. | 128/848 |
| 5,103,838 A | 4/1992 | Yousif | 128/859 |
| 5,203,701 A | 4/1993 | Burtch | 433/215 |
| 5,277,203 A | 1/1994 | Hays | 128/861 |
| 5,328,362 A | 7/1994 | Watson et al. | 433/6 |
| 5,447,168 A | 9/1995 | Bancroft | 128/859 |
| 5,462,066 A | 10/1995 | Snyder | 128/848 |
| 5,511,562 A | 4/1996 | Hancock | 128/859 |
| 5,513,656 A | 5/1996 | Boyd, Sr. | 128/859 |
| D373,421 S | 9/1996 | Brown | D24/180 |
| 5,584,687 A | 12/1996 | Sullivan et al. | 433/6 |
| 5,692,523 A * | 12/1997 | Croll et al. | 128/859 |
| 5,718,575 A | 2/1998 | Cross, III | 433/6 |
| D397,442 S | 8/1998 | Kittelsen | D24/180 |
| 5,836,761 A | 11/1998 | Belvedere et al. | 433/6 |
| 5,865,619 A | 2/1999 | Cross, III et al. | 433/6 |
| 5,873,365 A | 2/1999 | Brown | 128/859 |
| D406,405 S | 3/1999 | Yoshida | D29/108 |
| 5,879,155 A | 3/1999 | Kittelsen | 433/6 |
| 5,921,240 A | 7/1999 | Gall | 128/848 |
| 5,931,164 A | 8/1999 | Kiely et al. | 128/859 |
| 6,012,919 A | 1/2000 | Cross, III et al. | 433/6 |
| 6,092,524 A | 7/2000 | Barnes, Sr. | 128/859 |
| 6,152,138 A | 11/2000 | Brown et al. | 128/859 |
| 6,371,758 B1 | 4/2002 | Kittelsen | 433/6 |

(Continued)

Primary Examiner — Patricia Bianco
Assistant Examiner — Victoria J Hicks
(74) Attorney, Agent, or Firm — Greenberg Traurig, LLP; David J. Dykeman; Daniel T. Abramson

(57) ABSTRACT

A flexible dental appliance a left posterior occlusal pad having a base and an outer wall including a plurality of loops; a right posterior occlusal pad having a base and an outer wall including a plurality of loops; and a support bridge between the left posterior occlusal pad and the a right posterior occlusal pad. The plurality of loops create gaps in the outer wall and extend over a buccal aspect of the teeth of an upper jaw for enhancing retention of the dental appliance. The plurality of loops engage the teeth at interproximal spaces and cementoenamel junctions.

15 Claims, 5 Drawing Sheets

U.S. PATENT DOCUMENTS

| | | |
|---|---|---|
| 6,415,794 B1 | 7/2002 | Kittelsen et al. ............... 128/859 |
| 6,491,036 B2 | 12/2002 | Cook ............................ 128/859 |
| 6,553,996 B2 | 4/2003 | Kittelsen et al. ............... 128/859 |
| 6,581,604 B2 | 6/2003 | Cook ............................ 128/859 |
| 6,584,978 B1 | 7/2003 | Brett et al. .................... 128/859 |
| 6,588,430 B2 | 7/2003 | Kittelsen et al. ............... 128/859 |
| 6,626,180 B1 | 9/2003 | Kittelsen et al. ............... 128/859 |
| 6,691,710 B2 | 2/2004 | Kittelsen et al. ............... 128/859 |
| 6,820,623 B2 | 11/2004 | Cook ............................ 128/859 |
| D504,744 S | 5/2005 | Hidalgo et al. ............... D29/108 |
| 7,192,273 B2* | 3/2007 | McSurdy, Jr. ..................... 433/6 |
| 7,500,851 B2* | 3/2009 | Williams ........................... 433/7 |
| 2003/0205234 A1 | 11/2003 | Bardach et al. ............... 128/861 |
| 2005/0032015 A1* | 2/2005 | McSurdy, JR. ................... 433/7 |
| 2006/0096602 A1* | 5/2006 | Brown .......................... 128/861 |

\* cited by examiner

FLEXIBLE DENTAL APPLIANCE

RELATED APPLICATIONS

This application claims the benefit of U.S. Provisional Application Ser. No. 60/845,789, filed on Sep. 19, 2006, the entirety of which is hereby incorporated herein by reference for the teachings therein.

FIELD

The embodiments disclosed herein relate to dental appliances, and more particularly to a flexible dental appliance and methods of fabricating a flexible dental appliance.

BACKGROUND

Bruxism, commonly known as tooth grinding, is the clenching together of the bottom and upper jaw accompanied by the grinding of the lower set of teeth with the upper set. Bruxism affects between 10-50% of the population. Although bruxism can occur during the waking hours, bruxism most frequently occurs at night while sleeping. During sleep, the biting force (the force at which the jaws clench together) can be up to six times greater than the pressure during waking hours. Consequently, nighttime bruxism is more likely to cause significant damage.

Bruxism can lead to pain and cause damage to gums and other oral structures including: sore facial muscles, headaches, and ear-aches; cosmetic damage to teeth; sensitive teeth; fractured teeth and fillings; and temperomandibular joint damage. The muscles used to chew food are the same ones responsible for bruxism. Consequently, the chewing muscles often feel sore or tender in the morning. The clenching may make the jaw feel tight or may cause pain when the sides of the mouth are touched. Often this muscle pain manifests itself as a headache, ear-ache, or neck pain. Bruxism can cause the teeth to be ground down becoming significantly shortened and creating cosmetic damage. As the enamel of the tooth is worn away by bruxism the underlying dentin layer of the tooth is exposed and the tooth may become sensitive to cold, pressure, and other stimuli. The high pressure created from bruxism can fracture teeth and crack fillings. Bruxism can cause damage to the temperomandibular joint, which is the "hinge" which connects the lower jaw to the upper jaw allowing people to chew and talk.

Prior art dental appliances and mouth guards have attempted to reduce the complications associated with bruxism. The mouth guards try to absorb the punishment that the teeth would normally endure during bruxism and minimize the damage associated with bruxism. Prior art techniques for reducing clenching stress are described in U.S. Pat. No. 5,513,656 entitled "Intraoral semi-custom discluder device;" U.S. Pat. No. 5,584,687 entitled "Performance Enhancing Dental Appliance;" U.S. Pat. No. 6,581,604 entitled "Low-Density Polyethylene Dental Appliance and Mouthguard;" and U.S. Pat. No. 6,584,978 entitled "Mouthguard and method of making," all of which are hereby incorporated by reference in their entireties for the teachings therein.

Prior art mouth guards have been composed with materials that may be harmful to users, do not effectively prevent the complications associated with bruxism, and do not remain in the user's mouth, especially during wear at nighttime. Prior art mouth guards have been made of ethylene vinyl acetate (EVA) which is subject to degradation due to the user clenching and chewing on the appliance or mouth guard. Upon decomposition, EVA will break down to hazardous vinyl acetate, acetic acid, carbon monoxide and hazardous hydrocarbon oxidation products. Prior art mouth guards do not prevent bruxism; they treat damage to the teeth during bruxism. Therefore, there remains a need in the art for a safe, comfortable, and effective custom-fitting dental appliance that provides relief for the common complications associated with bruxism while relaxing the muscles so that bruxism is prevented from occurring.

SUMMARY

A flexible dental appliance that is custom-fit to a mouth of a user is disclosed herein.

According to aspects illustrated herein, there is provided a dental appliance including a left posterior occlusal pad having a base and an outer wall including a plurality of loops; a right posterior occlusal pad having a base and an outer wall including a plurality of loops; and a support bridge between the left posterior occlusal pad and the a right posterior occlusal pad.

According to aspects illustrated herein, there is provided a mouth guard for treating bruxism including a left occlusal pad that includes a base having has a top surface with a plurality of indentations, a labial wall extending from the base, and a lingual wall extending from the base and having a plurality of loops; a right occlusal pad that includes a base having a top surface with plurality of indentations, a labial wall extending from the base, and a lingual wall extending from the base and having a plurality of loops; and a support bridge connecting the left occlusal pad and the right occlusal pad, wherein the left occlusal pad and the right occlusal pad raise an occlusal plane, creating disclusion.

According to aspects illustrated herein, there is provided a method of fabricating a dental appliance including forming a dental impression of a mouth including an upper jaw and a lower jaw; filling the dental impression with a plaster material to create a master mold of the mouth including the upper jaw and the lower jaw; duplicating the master model using a reversible hydrocolloid material to create a working model including the upper jaw and the lower jaw; waxing occlusal surfaces of posterior teeth of the upper jaw to obtain a left occlusal pad and a right occlusal pad, each pad having: a base having a top surface with teeth indentations for receiving the posterior teeth of the upper jaw, and inner walls and outer walls extending upward; connecting the left occlusal pad and the right occlusal pad using the palatal strap; and creating a plurality of loops on the outer walls that extend over a buccal aspect of the posterior teeth.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
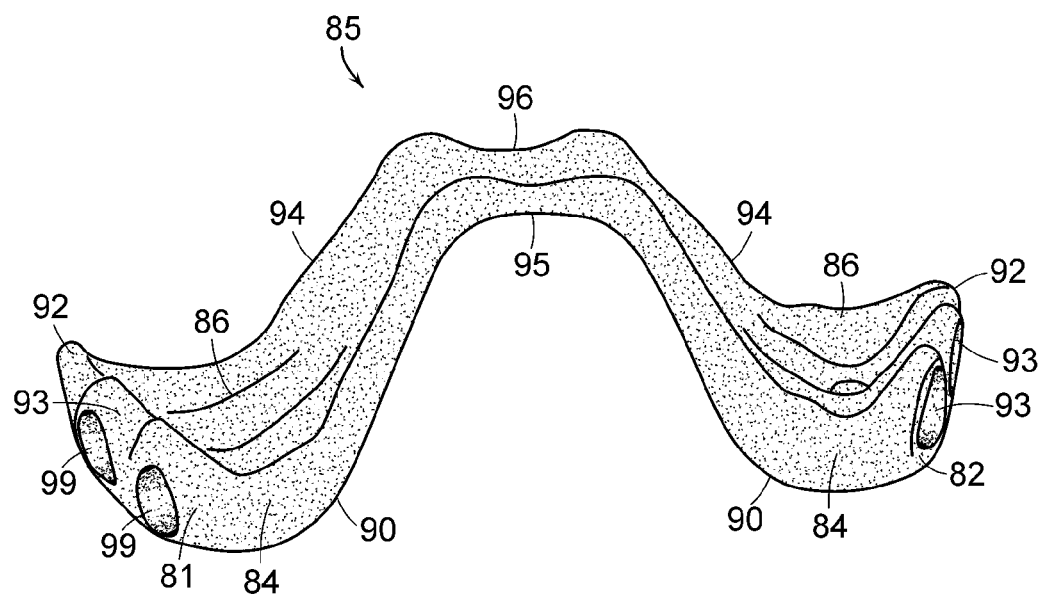
FIG. 1 is a perspective view of a dental appliance of the presently disclosed embodiments.
Figure 2:
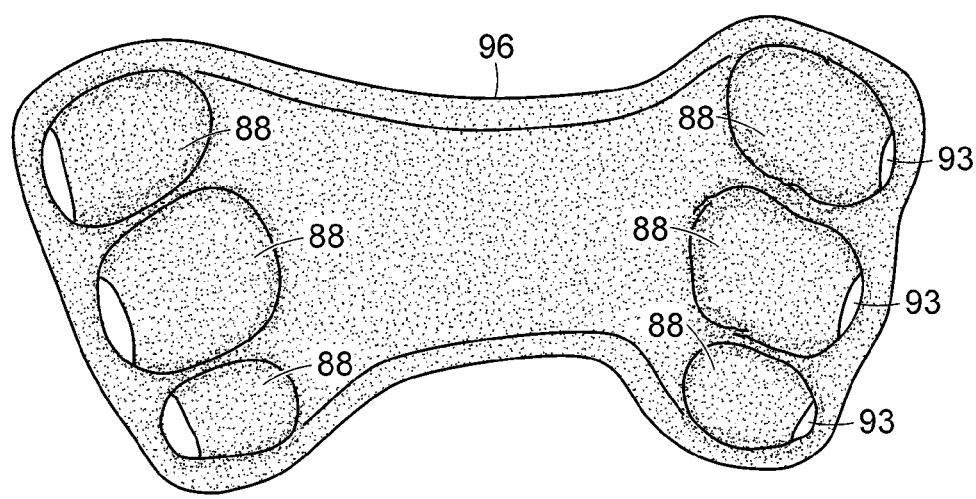
FIG. 2 is top view of a dental appliance of the presently disclosed embodiments.
Figure 3:
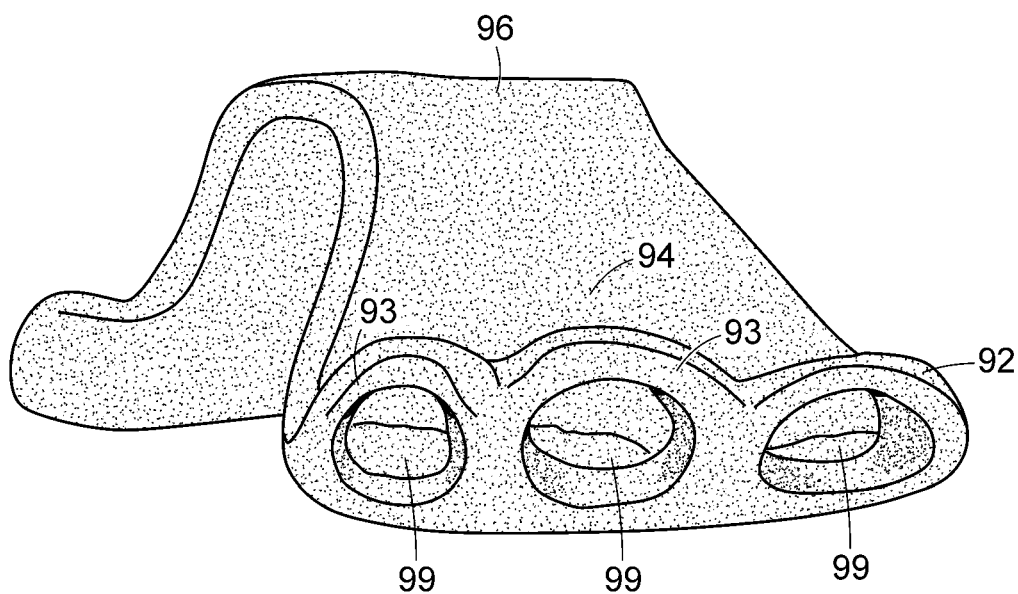
FIG. 3 is a side view of a dental appliance of the presently disclosed embodiments.

A flexible custom-fitting dental appliance of the presently disclosed embodiments is disclosed generally at 85 in FIG. 1. The dental appliance 85 treats bruxism and other conditions, disorders or diseases of the mouth. FIG. 1 shows a perspective view of the dental appliance 85. FIG. 2 shows a top view of the dental appliance 85. FIG. 3 shows a side view of the dental appliance 85.

The dental appliance 85 includes a left posterior occlusal pad 82 having a base 84 and an outer wall 92 including a plurality of loops 93; a right posterior occlusal pad 81 having a base 84 and an outer wall 92 (labial wall) including a plurality of loops; and a support bridge 96 between the left posterior occlusal pad 82 and the a right posterior occlusal pad 81.

The dental appliance 85 comprises two posterior occlusal pads, a left posterior occlusal pad 82 and a right posterior occlusal pad 81, and a connecting portion or support bridge 96 that extends and connects respective inner walls 94 (lingual walls) of the left occlusal pad 81 and the right occlusal pad 82. The support bridge 96 is also referred to as a palatal strap 96.

The dental appliance 85 actively engages the posterior teeth when placed in a mouth of a user, thus providing a custom-fit. The dental appliance 85 flexes upon insertion, effectively snapping into place, then returning to a passive state. The posterior occlusal pads 81 and 82 raise the occlusal plane where the upper and the lower teeth meet, creating disclusion. By creating disclusion the stress to the teeth, muscles, and joints are relieved and absorbed by the dental appliance 85. The support bridge 96 connects the posterior occlusal pads 81 and 82 together within the mouth and out of the way of the tongue to maintain the position of the occlusal posterior pads 81 and 82 within the mouth during use and to prevent loss of the pads 81 and 82 such as by swallowing. The support bridge 96, and the two maxillary posterior occlusal pads 81 and 82 act as retention system.

The posterior occlusal pads 81 and 82 include a base 84 having a fitted top surface 86 with custom-fit teeth indentations 88 (best shown in FIG. 2) for receiving the posterior teeth of the upper jaw. The base 84 has a bottom surface 90 that may be smooth. Extending upwardly from the base 84 are labial walls 92 and the lingual walls 94. The labial walls 92 are interrupted by a plurality of loops 93 that extend over the buccal aspect of each of the posterior teeth for enhancing retention of the dental appliance 85 within a user's mouth. The loops 93 arch, such that the angle of the arch conforms to the buccal aspect of the posterior teeth. The loops 93 shape conforms to the infrabulge area, that portion of the crown of the tooth gingival to the height of contour. In an embodiment, the boundaries of the loops 93 touch the interproximal space between the posterior teeth and the cementoenamel junction (CEJ). The loops 93 have a thickness ranging from about 1.5 millimeters to about 3.0 millimeters, although those skilled in the art will recognize that the loops can have a greater or lesser thickness and still be within the spirit and scope of the presently disclosed embodiments. In an embodiment, the thickness of the loops 93 is about 2.5 millimeters.

The plurality of loops 93 create gaps 99 in the outer wall and extend over a buccal aspect of the teeth of an upper jaw for enhancing retention of the dental appliance. The gaps 99 may be large or small and may vary in size from tooth to tooth. The plurality of loops 93 engage the teeth at interproximal spaces and cementoenamel junctions. In an embodiment, the plurality of loops 93 may correspond to each tooth engaging the outer wall 92. In an embodiment, the plurality of loops 93 are only present for some teeth that the outer wall 92 engages and some teeth have a solid outer wall 92 without gaps.

Each loop 93 engages a tooth to prevent dislodging of the appliance 85. With the loops 93, the dental appliance 85 remains stable during all lateral, protrusive, eccentric and parafunctional movement of the mandibular jaw, in relation to the maxillary jaw, when the upper and lower teeth come into contact during these motions. The loops 93 keep the appliance 85 engaged to the teeth and the appliance 85 does not fall out of the patient's mouth.

The connecting portion or continuous support bridge 96 is shaped as to lie along the palate of the mouth and out of the way of the tongue. The support bridge 96 may be tapered along a central portion 95, thus reducing the weight of the appliance and minimizing contact with the palate and with the tongue. The support bridge 96 connects the posterior occlusal pads 81 and 82 together within the mouth and out of the way of the tongue to maintain the position of the occlusal pads 81 and 82 within the mouth during use and to prevent loss of the occlusal pads 81 and 82 such as by swallowing.

The dental appliance 85 is fabricated using a model record of each user, giving the dental appliance 85 a custom fit. A model record is a plaster cast of the upper and lower jaws that is created of both the maxillary and mandibular dentition using a dental impression material including, but not limited to alginate, hydrocolloid, polyvinyls, and other similar impression materials known to those skilled in the art. A standard dental impression tray is used for the appropriate patient size and dental arch. The impression is used as a negative to create a positive plaster cast of the patient's upper and lower dentition.

The dental appliance 85 is composed of a material that should be strong, elastic, abrasion resistant, lustrous, resilient, washable, resistant to damage from oil and chemicals, light weight, and will not wear the user's teeth. The dental appliance 85 may be pre-colored. In an embodiment, the dental appliance 85 includes a flexible material system composed of a uniform material allowing complete interoral compatibility. In an embodiment, the dental appliance 85 is fabricated from a polyamide (PA) material. In an embodiment, the polyamide material is a thin walled biocompatible nylon thermoplastic resin. A suitable polyamide material is Flexite Plus which is commercially available from The Flexite Company in Mineola, N.Y.

Figure 4:
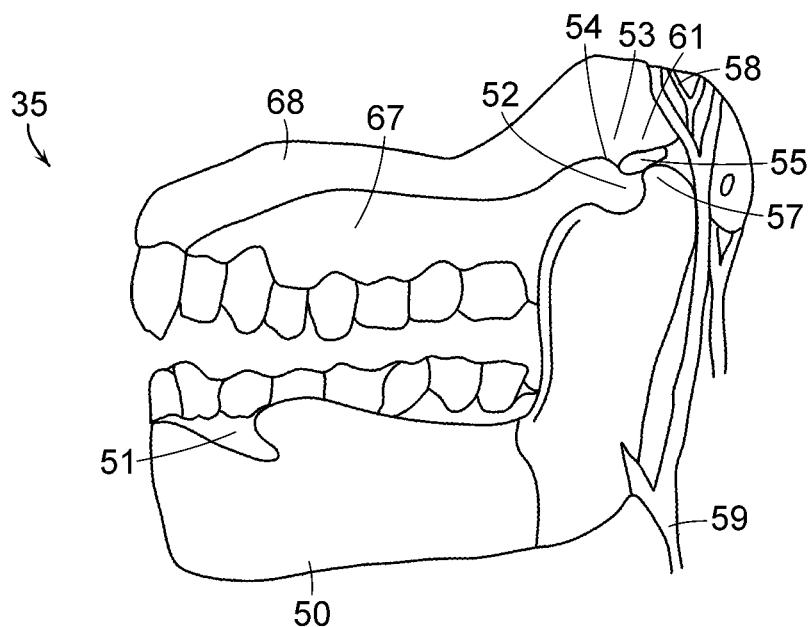
FIG. 4 is a side view of a jaw and a temperomandibular joint.

FIG. 4 shows a side view of a mouth 35 of a user of the dental appliance 85 of the presently disclosed embodiments. The mouth 35 generally comprises a rigid upper jaw, known as a maxilla 68, and a moveable lower jaw, known as a mandible 50, which are movably connected at the temperomandibular joint (TMJ) 52. More specifically, the rigid upper jaw 68 has gum tissue 67 within the mouth 35. Gum tissue 67, as well as the bone thereunder, supports anterior teeth (incisors and canines) which have incisal or biting surfaces. The gum tissue 67 and the bone thereunder also support posterior teeth (molars and bicuspids) which have cusps or biting surfaces. The movable jaw 50 supports a bone covered by gum tissue 67 which further supports anterior teeth (incisors and canines) with incisal or biting surfaces and posterior teeth (molars and bicuspids) with occlusal biting surfaces.

A temporal bone 53 is located above and rearward of the mandible 50 and an articular eminence 54 forms the beginning of the socket of the TMJ 52, with a cartilage 55 located rearward and posteriorly to the articular eminence 54. A condyle 57 of the mandible 50 forms the ball of the TMJ 52. A glenoid fossa 61 is a deep concavity in the temporal bone 53 that receives the condyle 57 of the mandible 50. An auriculotemporal nerve 58, a nerve that influences sensory and motor activities of the body, and a supra-temporo artery 59, an artery that provides blood circulation to the head, pass through the TMJ 52.

Figure 5:
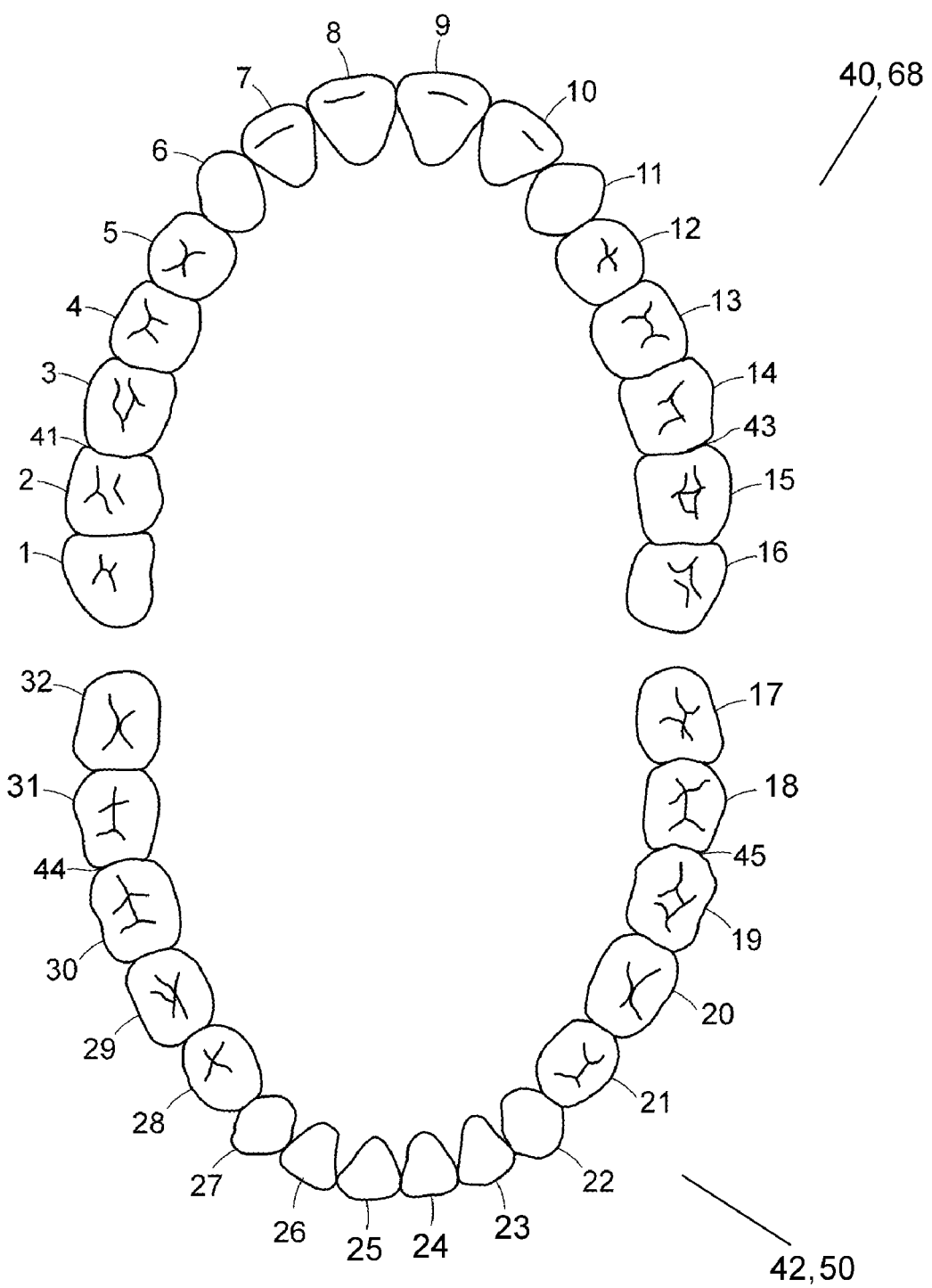
FIG. 5 is a drawing of an upper set of teeth of a maxilla and a lower set of teeth of a mandible.

FIG. 5 shows a view of an upper set of teeth 40 of the maxilla 68 and a lower set of teeth 42 of the mandible 50. FIG. 5 is an embodiment of a teeth structure. The teeth structure of various individuals can differ from the embodiment shown in FIG. 5 and still be within the spirit and scope of the presently disclosed embodiments. Both the upper set of teeth 40 and the lower set of teeth 42 comprise molars, bicuspids, cuspids, and incisors. More particular, the upper set of teeth 40 in a right side 41 of the maxilla 68 comprises a third molar 1, a second molar 2, a first molar 3, a second bicuspid 4, a first bicuspid 5, a cuspid 6, a lateral incisor 7 and a central incisor 8. Continuing from the central incisor 8 on a left side 43 of the maxilla 68 are a central incisor 9, a lateral incisor 10, a cuspid 11, a first bicuspid 12, a second bicuspid 13, a first molar 14, a second molar 15 and a third molar 16. The lower set of teeth 42 in a left side 45 of the mandible 50 comprise a third molar 17, a second molar 18, a first molar 19, a second bicuspid 20, a first bicuspid 21, a cuspid 22, a lateral incisor 23 and a central incisor 24. Continuing from the central incisor 24 on a right side 44 of the mandible 50 are a central incisor 25, a lateral incisor 26, a cuspid 27, a first bicuspid 28, a second bicuspid 29, a first molar 30, a second molar 31 and a third molar 32.

Figure 6:
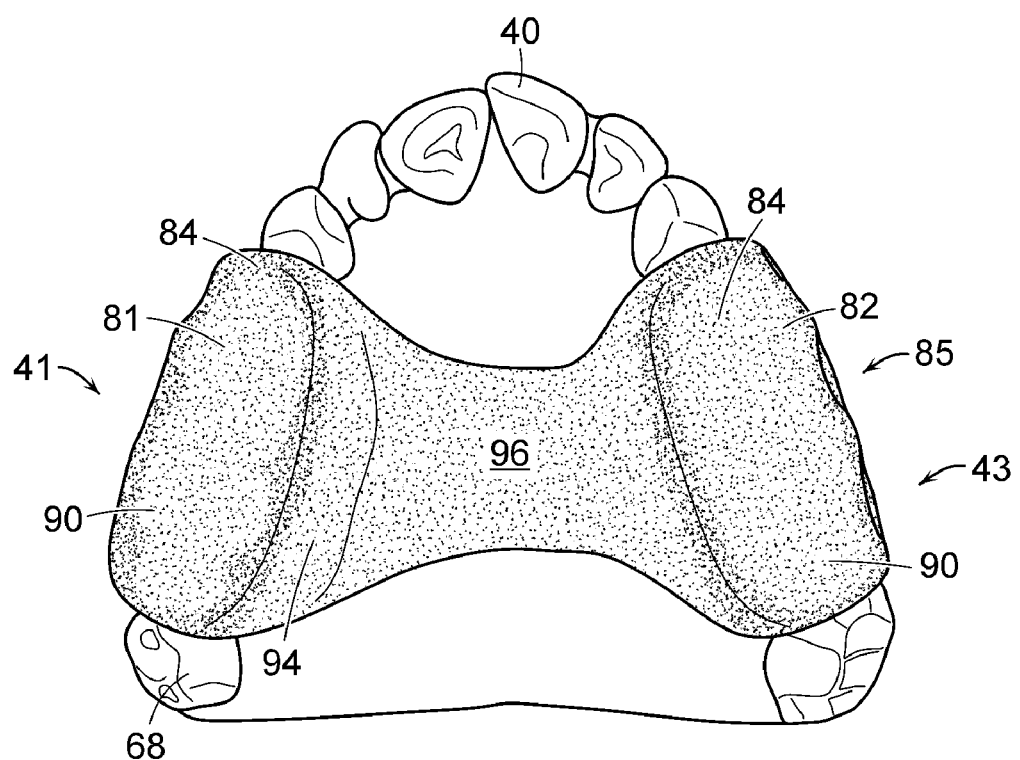
FIG. 6 is a bottom plan view of a model of an upper set of teeth with a dental appliance of the presently disclosed embodiments covering the maxillary posterior teeth.

FIG. 6 shows a bottom plan view of a model of an upper set of teeth 40 with a dental appliance 85 of the presently disclosed embodiments covering the maxillary posterior teeth. The dental appliance 85 flexes upon insertion effectively snapping into place, and then returning to a passive state. The flexibility of the dental appliance 85 allows the dental appliance 85 to expand over the contours of the upper set of teeth 40 and "snap" into the infrabulge on the buccal aspect of the upper set of teeth 40. The dental appliance 85 actively engages the posterior teeth when placed in the mouth 35 of a user. In an embodiment, the dental appliance 85 covers the upper set of teeth 40 in the right side 41 of the maxilla 68 at the first molar 3, the second bicuspid 4, and the first bicuspid 5 (covered by the dental appliance in FIG. 6). On the left side 43 of the maxilla 68, the dental appliance 85 covers the first bicuspid 12, the second bicuspid 13, and the first molar 14 (covered by the dental appliance in FIG. 6).

Figure 7:
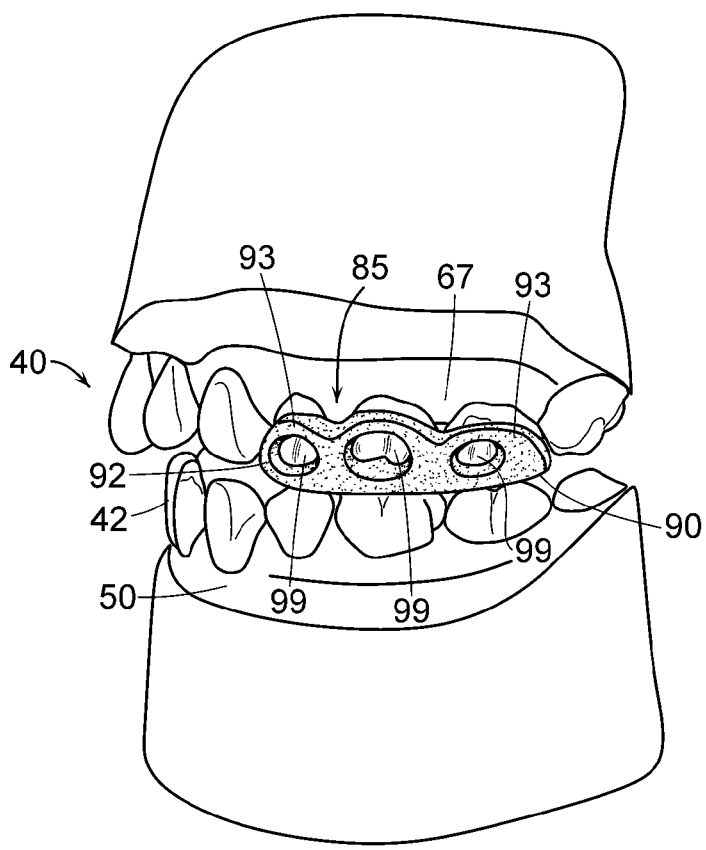
FIG. 7 is a model of an upper set of teeth and a lower set of teeth with a dental appliance of the presently disclosed embodiments covering the maxillary posterior teeth during a standard bite of a patient.
Figure 8:
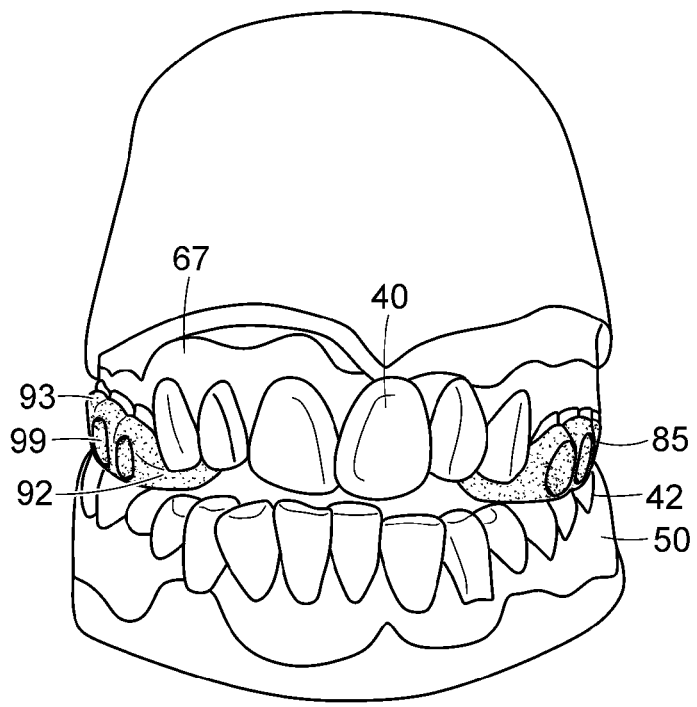
FIG. 8 is a model of an upper set of teeth and a lower set of teeth with a dental appliance of the presently disclosed embodiments covering the maxillary posterior teeth during a standard bite of a patient.

FIG. 7 and FIG. 8 show models of the upper set of teeth 40 with the dental appliance 85 covering at least a portion of the occlusion surface of several lower teeth 42 of the mandible 50 during a representative bite of a user. Each posterior occlusal pad 81 and 82 includes the base 84 and the bottom surface 90 that may be smooth. The posterior pads 81 and 82 raise the occlusal plane creating disclusion. By creating disclusion, the stress to the teeth, muscles and joints is relieved and absorbed by the flexible dental appliance 85. The loops 93 are visibly positioned over the posterior teeth. The tops of the labial walls 92 lie below the gum tissue 67 and rest on the posterior teeth. The loop 93 design provides maximum interoral retention of the dental appliance 85 along with user compliance and comfort. The user is unable to dislodge the dental appliance 85 when grinding or clenching of the teeth, especially while sleeping. The full loop 93 design prevents the dislodging of the appliance 85 when the user is bruxing.

In an embodiment, the posterior occlusal pads 81 and 82 are positioned bilaterally on maxillary molars 3 and 14, and bicuspids 4, 5, 12 and 13. In an embodiment, the dental appliance 85 has posterior occlusal pads 81 and 82 having a thickness of about 1.5 mm to about 2.0 mm, and the support bridge 96 has a thickness of about 1.5 mm; width of about 10 mm; and a length of about 22 mm. The labial wall 92 is interrupted by the loops 93 that extend over the buccal aspect of the maxillary molars 3 and 14, and bicuspids 4, 5, 12 and 13. In an embodiment, the plurality of loops 93 have a thickness of about 1.5 mm. The destructive efforts of bruxism are eliminated by distribution of the load to the maximum number of approximately equal intensity posterior tooth contacts. By using these specifications the signs and symptoms of bruxism are minimized. Those skilled in the art will recognize that the thickness specifications can be increased or decreased and still be within the spirit and scope of the presently disclosed embodiments.

In an embodiment, the dental appliance 85 is made of a flexible polyamide material which allows the dental appliance 85 to actively engage the posterior teeth, raising the occlusal plane, creating disclusion. The disclusion relieves the stress of the teeth, muscles and joints by relieving the stress to these areas, the signs and symptoms of bruxism are effectively treated. When placed in the mouth of a user, the dental appliance 85 actively engages the posterior teeth although once engaged it returns to a passive state. The dental appliance 85 is designed on a plaster model in a passive state with the previously described position of the loops 93, occlusal pads 81 and 82, and palatal strap 96. The dental appliance 85 is designed to rest on the teeth and the hard palate with no force, thus passive. The dental appliance 85 is in a flexible state when it is flexing over the suprabulge of the buccal aspect of the teeth during placement of the dental appliance 85. After clearing the suprabulge on the buccal aspect, the loops 93 rest passively against the infrabulge of the teeth and lock the dental appliance 85 into place. This provides the user with comfort that they will not choke or swallow the dental appliance 85 while sleeping.

The dental appliance 85 is thin and able to be worn during the day as well. The user can function normally with the dental appliance 85 placed in the mouth. The custom mold of the dental appliance 85 permits a tight fit on a user's palate that allows the user to wear the dental appliance 85 while talking. The dental appliance 85 is specially designed for phonetic purposes, allowing the user to communicate while wearing the dental appliance 85. In addition, the dental appliance 85 does not affect the ability of a person to drink liquids and does not interfere with breathing.

The flexible dental appliance 85 reduces the stimulus to the nerves helping to decrease the amount of bruxism. When the hard surfaces of the opposing dentition come into contact, these hard surfaces produce a positive stimulus to the nerves of the teeth. This positive stimulus reinforces the act of bruxism. By separating the opposing dentition, the flexible dental appliance 85 decreases the stimulus to the nerves reducing bruxism.

Those skilled in the art will recognize that the dental appliance 85 of the presently disclosed embodiments may be used to prevent and/or treat various conditions and diseases of the mouth. The dental appliance 85 may be used to prevent cracking of tooth enamel; development of bony tuberosity; erosion of the tooth enamel; wearing or breaking of fillings in the mouth; breaking of porcelain crowns; movement of teeth; gingival recession; cheek irritation; headaches; temperomandibular joint pain; earaches; insomnia; depression and eating disorders. The dental appliance 85 may be further used to treat cold sensitive teeth; trismus of the jaw; erosion of the tooth enamel; wearing or breaking of fillings in the mouth; loose teeth; movement of teeth; gingival recession; muscle hyperactivity; abrasive wear of the teeth; periodontal pockets; enlarged masseter muscle; cheek irritation; headaches; temperomandibular joint pain; earaches; insomnia; depression and eating disorders.

When the hard enamel surfaces of the teeth come together the pressure of the jaw produces interoral cracking of the dental enamel. The dental appliance 85 absorbs the stress of the jaw muscle and prevents cracking of the tooth enamel, wearing or breaking of fillings and fracturing of porcelain crowns. The dental appliance 85 absorbs the pressure placed on the teeth by the jaw and thus relieves the stress to the teeth. When the mandibular jaw is putting constant pressure or tension against the maxillary jaw, it weakens the periodontal ligaments and results in movement of the teeth. This tension is also transmitted to the gums, which in turn respond by receding. The dental appliance 85 absorbs the pressure or tension in these areas which prevents gingival recession and the movement of the teeth.

The occlusal pads 81 and 82 provide a platform which prevents cheek irritation. Headaches are effectively treated because the pressure exerted by the jaw muscle is absorbed by the dental appliance 85 and not transmitted to the temporallis muscle. Earaches can be caused by stress on the temporomandibular joint which the dental appliance 85 effectively absorbs, preventing earaches. Insomnia and depression are also treated by the dental appliance 85. Insomnia can be caused by tension in the head, neck and jaw. Not getting enough sleep can result in depression. The dental appliance 85 treats both insomnia and depression by absorbing stress which causes the lack of sleep. Eating disorders can result in sore or cracked teeth and sensitivity to hot and cold and pressure. The patient ends up with a very limited diet. The dental appliance 85 treats these conditions as well. When the teeth crack, this produces a leak in the enamel coating of the tooth, causing sensitivity. The dental appliance 85 does not allow the pressure from the jaw to crack the teeth in the first place.

Trismus of the jaw, or lock jaw and muscle hyperactivity are caused by the pressure exerted by the jaw muscles. Periodontal pockets and an enlarged masseter muscle are a result of constant tension on the teeth. All are treated by absorbing the pressure with the appliance. Finally, during bruxing the gums and enamel become weak from the constant motion between the upper and lower teeth, causing erosion of tooth enamel and loose teeth. The dental appliance 85 can prevent erosion and loose teeth because the posterior pads create disclusion, not allowing the teeth to touch, thus not wearing and not moving.

A method of fabricating a dental appliance 85 includes, but is not limited to, the steps described below. First, a dental impression is made of a user's mouth using impression materials and techniques known to those skilled in the art. For example, a dentist will dry off a patient's teeth (by way of blowing air on them), followed by placing impression paste on and around each tooth. Next, a tray holding more impression material (an impression tray) is placed up over the teeth and held in place for a few minutes until both portions of impression material have set and become fused. The tray and impression material are then removed from the patient's mouth as a single unit. The dental impression is used to create a plaster mold of the patient's mouth and teeth.

The impression is then filled with a plaster material to create a replica of the user's mouth including teeth and surrounding gum tissue over which the dental appliance 85 will be fitted. The plaster material should reproduce the finest details of the impression, with thixotropic properties to facilitate handling, thus creating a master model. The plaster material should have high compatibility with all impression materials to ensure casts with excellent surface texture and be extremely hard when dry. Those skilled in the art will recognize that various dental plaster materials known in the art are within the spirit and scope of the presently disclosed embodiments.

The lingual gingival margin is that area of the teeth closest to the hard palate. The lingual gingival margin is blocked out by using a hard dental block out wax. This area of the teeth has an undercut which would prevent the dental appliance 85 from sitting properly on the teeth.

The palatal strap is then scored on the master model of the upper jaw. Scoring refers to scraping a line from one pad to the next against the hard palate on the master model to a depth of about one millimeter. Scoring creates a post damming effect and increases the platform of the dental appliance 85 against the hard palate which increases stability of the dental appliance 85 without reducing patient compliance.

The master model is duplicated using a reversible hydrocolloid or other accurate material. The duplicate model is the fabrication model or a working model. The original model is kept for a frame of reference and in the end to see if the dental appliance 85 will fit properly.

The master model is then articulated opening the bite just enough to assure canine disclusion in all excursions. Canine occlusion during parafunctional movement of the upper jaw against the lower jaw produces a concentrated force against the smallest number of teeth, resulting in straining of the jaw muscles. Preventing this contact disclusion eliminates the strain. The posterior pads 81 and 82 raise the occlusal plane. The occlusal plane must be raised enough to prevent tripping of the canines during parafunctional movements.

The posterior bite is rebuilt by waxing the occlusal surfaces of involved teeth. Rebuilding the posterior teeth provides the necessary amount of polyamide nylon material which eliminates the stress or tension on the anterior teeth during bruxing. The dental appliance 85 should provide enough material to absorb the force of the jaw muscles and to create a smooth and flat surface to move against unobstructed.

The right and left sides of the dental appliance 85 are connected with a wax palatal strap. The wax palatal strap is the same size and dimensions as the final strap, minimum width of about 10 mm and a minimum length of about 20 mm. Wax is then used to create loops on all involved teeth. The wax acts as a template, and becomes the final shape of the dental appliance 85. The flexible resin material is processed as per manufactures specifications known to those skilled in art. For example, boiling out wax template with proper times and temperature; heating material to proper temperature; injecting material at correct times and temperature; and polishing and finishing material with appropriate abrasives.

A method of fabricating a dental appliance includes forming a dental impression of a mouth including an upper jaw and a lower jaw; filling the dental impression with a plaster material to create a master mold of the mouth including the upper jaw and the lower jaw; duplicating the master model using a reversible hydrocolloid material to create a working model including the upper jaw and the lower jaw; waxing occlusal surfaces of posterior teeth of the upper jaw to obtain a left occlusal pad and a right occlusal pad, each pad having: a base having a top surface with teeth indentations for receiving the posterior teeth of the upper jaw, and inner walls and outer walls extending upward; connecting the left occlusal pad and the right occlusal pad using the palatal strap; and creating a plurality of loops on the outer walls that extend over a buccal aspect of the posterior teeth.

The method of fabricating a dental appliance further includes blocking out the lingual gingival margin by using a hard dental block out wax. The method of fabricating a dental appliance further includes scoring a palatal strap on the upper jaw of the master model using wax. The method of fabricating a dental appliance further includes replacing the wax material of the left occlusal pad, right occlusal pad, the plurality of loops, and the palatal strap with a flexible polyamide material.

Those skilled in the art will recognize that the steps may be performed in any order and a different order than listed above and still be within the spirit and scope of the presently disclosed embodiments. Those skilled in the art will recognize that steps may be removed or added to the above steps and still be within the spirit and scope of the presently disclosed embodiments.

A custom dental appliance comprises two maxillary posterior occlusal pads and connected with a connective supportive bridge. The dental appliance actively engages the posterior teeth when placed in the mouth. The dental appliance flexes upon insertion, effectively snapping into place, then returning to a passive state. The posterior occlusal pads raise the occlusal plane creating disclusion. By creating disclusion the stress to the teeth, muscles, and joints are relieved and absorbed by the dental appliance. The supportive bridge is provided connecting the posterior occlusal pads together within the mouth and out of the way of the tongue to maintain the position of the posterior occlusal pads within the mouth during use and to prevent loss of the occlusal pads such as by swallowing.

The dental appliance consists of bilateral posterior occlusal pads bridged together using a supportive bridge. The advantages of the dental appliance of the presently disclosed embodiments include, but are not limited to, a flexible material system, which is of uniform material allowing complete interoral compatibility, and in the posterior occlusal pad retention system.

In an embodiment, the supportive portion or continuous vertical supportive bridge may be fabricated from a material that is different than the material of the posterior occlusal pads. In an embodiment, the supportive portion is fabricated from a metal material, and the occlusal pads are fabricated from a flexible material. In an embodiment, the metal material is a basic alloy like chromecobalt which is the standard material used in metal palatal straps of dental appliances. In an embodiment, the metal material is gold. The flexible material of the occlusal pads may be injected into the loops that are designed into the metal supportive portion and finished to a smooth tapering feathered edge.

In an embodiment, the labial walls are interrupted by clasps, rather then loops, that form a "J-shape" and that extend over the buccal aspect of each of the posterior teeth for enhancing retention of the dental appliance within a user's mouth. The J-shape clasps may be brought up into the interproximal space between the posterior teeth and then turn along the cementoenamel junction (CEJ). The "J" loop design holds the dental appliance to the teeth during normal bruxing. Intensive episodes of bruxing may require the full loop embodiment to keep the appliance from dislodging.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A dental appliance comprising:
   a left posterior occlusal pad having a base with a smooth bottom surface and an outer sidewall including a plurality of open faced closed loops creating holes entirely through the outer sidewall, wherein an entire loop is adapted to directly engage posterior teeth of an upper jaw of a user, and wherein each of the plurality of loops forms an arch having an angle adapted to conform the plurality of loops to the buccal aspect of the posterior teeth to retain the dental appliance;
   a right posterior occlusal pad having a base with a smooth bottom surface and an outer sidewall including a plurality of open faced closed loops creating holes entirely through the outer sidewall, wherein an entire loop is adapted to directly engage posterior teeth of an upper jaw of the user, and wherein each of the plurality of loops forms an arch having an angle adapted to conform the plurality of loops to the buccal aspect of the posterior teeth to retain the dental appliance; and
   a support bridge between the left posterior occlusal pad and the right posterior occlusal pad adapted to lie along a palate of the user.

2. The dental appliance of claim 1 further comprising a top surface of the base including a plurality of indentations for accommodating teeth.

3. The dental appliance of claim 1 wherein the plurality of loops are adapted to extend over a buccal aspect of the teeth of the upper jaw for enhancing retention of the dental appliance.

4. The dental appliance of claim 1 wherein the support bridge connects an inner wall of the left posterior occlusal pad and an inner wall of the right posterior occlusal pad.

5. The dental appliance of claim 1 wherein the plurality of loops are adapted to engage the teeth at interproximal spaces and cementoenamel junctions.

6. The dental appliance of claim 1 adapted to custom fit the user.

7. The dental appliance of claim 1 wherein the appliance is composed of a uniform material.

8. The dental appliance of claim 1 wherein the appliance is composed of a flexible polyamide material.

9. The dental appliance of claim 1 for use in the treatment of bruxism.

10. The dental appliance of claim 1 wherein the left posterior occlusal pad and the right posterior occlusal pad are adapted to separate occlusal surfaces of the teeth.

11. The dental appliance of claim 1 wherein the left posterior occlusal pad and the right posterior occlusal pad are adapted to create disclusion.

12. A mouth guard for treating bruxism comprising:

a left occlusal pad that includes a base having a top surface with a plurality of indentations and a bottom smooth surface, a labial wall extending from the base, and a lingual sidewall extending from the base and having a plurality of open faced closed loops creating holes entirely through the lingual sidewall, wherein an entire loop is adapted to directly engage posterior teeth of an upper jaw of a user, and wherein each of the plurality of loops forms an arch having an angle adapted to conform the plurality of loops to a buccal aspect of the posterior teeth to retain the mouth guard;

a right occlusal pad that includes a base having a top surface with plurality of indentations and a bottom smooth surface, a labial wall extending from the base, and a lingual sidewall extending from the base and having a plurality of open faced closed loops creating holes entirely through the lingual sidewall, wherein an entire loop is adapted to directly engage posterior teeth of an upper jaw of the user, and wherein each of the plurality of loops forms an arch having an angle adapted to conform the plurality of loops to a buccal aspect of the posterior teeth to retain the mouth guard; and a support bridge connecting the left occlusal pad and the right occlusal pad adapted to lie along a palate of the user, wherein the left occlusal pad and the right occlusal pad are adapted to separate occlusal surfaces of the teeth, creating disclusion.

13. The mouth guard of claim 12 wherein the plurality of loops are adapted to extend over a buccal aspect of the teeth of the upper jaw for enhancing retention of the mouth guard.

14. The mouth guard of claim 12 wherein the plurality of loops are adapted to engage the teeth at interproximal spaces and cementoenamel junctions.

15. The mouth guard of claim 12 wherein creating disclusion is capable of reducing stress to teeth, muscles, and joints of a user.

* * * * *

UNITED STATES PATENT AND TRADEMARK OFFICE
CERTIFICATE OF CORRECTION

PATENT NO. : 8,201,560 B2
APPLICATION NO. : 11/901818
DATED : June 19, 2012
INVENTOR(S) : Jay L. Dembro Page 1 of 1

It is certified that error appears in the above-identified patent and that said Letters Patent is hereby corrected as shown below:

(74) Attorney, Agent, or Firm - Greenberg Traurig, LLP; David J. Dykeman; Daniel T. Abramson Delete “Daniel”
  Insert --Danielle--.

Signed and Sealed this
Twenty-eighth Day of August, 2012

David J. Kappos
*Director of the United States Patent and Trademark Office*